United States Patent [19]
Kantrowitz et al.

[11] Patent Number: 5,139,508
[45] Date of Patent: Aug. 18, 1992

[54] SURGICAL TOOL

[75] Inventors: Adrian Kantrowitz, Auburn Hills; Paul S. Freed, Bloomfield Hills, both of Mich.

[73] Assignee: L-Vad Technology, Inc., Auburn Hills, Mich.

[21] Appl. No.: 796,040

[22] Filed: Nov. 20, 1991

[51] Int. Cl.⁵ ............................................. A61B 17/32
[52] U.S. Cl. ................................... 606/184; 606/172; 606/180
[58] Field of Search ............... 606/167, 170, 171, 172, 606/181, 182, 184, 185

[56] References Cited

U.S. PATENT DOCUMENTS

| | | | |
|---|---|---|---|
| 1,557,464 | 10/1925 | Mick | 606/184 X |
| 2,818,852 | 1/1958 | Kugler | 606/184 X |
| 3,512,519 | 5/1970 | Hall | 606/184 X |
| 3,515,128 | 6/1970 | McEvoy | 606/184 X |
| 4,630,597 | 12/1986 | Kantrowitz et al. | 128/1 D |
| 4,634,422 | 1/1987 | Kantrowitz et al. | 604/49 |

Primary Examiner—Randall L. Green
Assistant Examiner—Mary Beth O. Jones
Attorney, Agent, or Firm—Basile and Hanlon

[57] ABSTRACT

A surgical tool for forming a circular opening through the skin which is of smaller diameter at the outer skin surface than at the inner surface of the skin employs a trephine having a circular cutting edge. The trephine is inserted into a pocket surgically formed beneath the skin with its cutting surface facing the skin. A rod member is then inserted through the skin and threaded into the trephine. The rod member is attached to a spring biased plunger within a tool housing which is released from a ready position by withdrawal of a locking pin. Upon release of the plunger, the spring drives the plunger to drive the cutting edge of the trephine outwardly through the skin.

8 Claims, 1 Drawing Sheet

SURGICAL TOOL

BACKGROUND OF THE INVENTION

The present invention is directed to a surgical tool employed to cut a circular opening of a specific diameter through the skin of a patient in connection with the implanting of a percutaneous access device.

Percutaneous access devices, hereinafter PAD, are employed to provide a through-the-skin connection between an external device and some instrument or other device implanted within a patient's body. PAD's are employed on a long-term or permanent basis as, for example, to provide external pneumatic and electrical connections to an implanted left ventricle assist device or dynamic aortic patch of the type disclosed in U.S. Pat. No. 4,630,597. A PAD of the general type with which the present invention is concerned is disclosed in U.S. Pat. No. 4,634,422 and consists basically of a body having a circular flange which is implanted beneath the patient's skin and a projection which projects coaxially from one side of the flange outwardly through the patient's skin. Electrical or pneumatic leads from within the patient's body are led through a passage through the projection of the PAD to a point where they are accessible from the exterior of the patient's body.

As set forth in greater detail in U.S. Pat. No. 4,634,422, in order to implant the PAD, at some stage during the implantation procedure it is necessary to cut a circular opening through the patient's skin to provide a passage for the projection to which the connections to external devices will be made. The outer layer of skin—i.e. the epidermis—has a natural propensity to attempt to close this surgical opening, and in U.S. Pat. No. 4,634,422 there is described in detail a technique for firmly bonding the underlying dermal layer of skin to the sidewall of the projection to prevent the down growth of epidermis around the implanted device.

The formation of a bond between the dermal layer of skin and the projection of the PAD is a delicate and time-consuming operation which, as might be expected, requires a precise and uniform initial "fit" between the edge of the circular opening cut through the dermis and the outer periphery of the projection of the PAD. The diameter of the opening through the dermis may be closely matched to the outer diameter of the projection by selection of the appropriate size of the trephine employed to cut the opening through the skin. However, due to the resilience of the skin, the trephine does not cut an opening with truly cylindrical sidewalls, but instead produces an opening of a frusto-conical configuration with the large diameter end of the opening facing outwardly of the skin. In that the outer sidewall of the PAD projection typically is cylindrical or tapered upwardly with an opposite inclination to that of the opposed sidewall of the opening cut through the skin, the "fit" between the projection of the PAD and the upper or outermost portion of the dermal layer is loose where it has the greatest need to be tight, greatly increasing the possibility of delayed or inadequate bonding between the dermal layer and projection, as well as increasing the risk of development of infection.

The present invention provides a surgical tool operable to cut a circular opening through the skin of a patient whose diameter increases with depth from the exterior surface of the skin.

SUMMARY OF THE INVENTION

A surgical tool according to the present invention includes a hollow cylindrical housing open at one end and having a reduced diameter bore through an end wall at the opposite end of the housing. Within the housing, a piston-like plunger is slidably received and formed with an integral elongate rod projecting outwardly from the housing through the bore in the housing end wall. A compression spring is engaged between the plunger and housing end wall biassing the plunger in a direction tending to retract the projecting rod into the housing. The plunger is normally maintained at an inward end limit of movement within the housing by a plug member which projects into the open end of the housing. A locking pin extending through aligned diametrically extending bores in the housing sidewall and plug member releasably locks the plug member in a seated position which maintains the plunger at its inward end limit of movement relative to the housing with the plunger engaging spring at a maximum compression.

A hollow cylindrical cutter or trephine, sharpened at one edge to form a circular cutting edge of a specific diameter, has a relatively thick bottom wall at its opposite end formed with a central internally threaded bore by means of which the cutter may be threaded onto threads cut at the end of the plunger rod to attach the cutter to the rod with its cutting edge facing the end wall of the cylindrical housing.

In use, the cutter is detached from the rod and inserted into a pocket beneath the patient's skin with the cutting edge facing the skin. The threaded end of the rod is then inserted through a relatively small hole punched through the skin and threaded into the cutter which is held during this procedure, as by a hemostat or tweezers. After the cutter has been threaded onto the rod, the locking pin is withdrawn and the plunger is driven by the spring to retract the rod until the cutting edge engages the end wall of the housing. A washer-like seat may be mounted on the outside of the end wall of the housing to form a shearing edge cooperable with the cutting edge of the cutting element. Further, the upper end of the plunger may be formed with recesses or a groove and the bottom of the plug member may be formed with a projection or a screwdriver-like blade engageable within the recess in the plunger to enable a manual rotation of the plunger and cutter if necessary to finally sever the skin completely around the opening cut.

After the skin has been completely severed, the cutter may be withdrawn through the cut opening. Because the resiliency of the skin causes the diameter of the opening in the skin to become progressively reduced as the cutter moves through the skin, the opening cut by the tool described above is formed with a frusto-conical shaped sidewall whose minimum diameter is at the outer surface of the skin.

The simple construction of the tool enables it to be economically manufactured for a one-time use - that is, the tool is a disposable tool.

Other objects and features of the invention will become apparent by reference to the following specification and to the drawings.

DESCRIPTION OF THE PREFERRED EMBODIMENT

Figure 3:
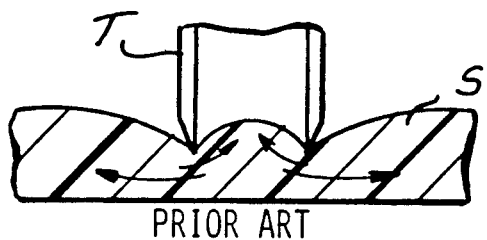
FIG. 3 is a diagrammatic view of a conventional method for forming a circular opening through the skin of a patient.
Figure 4:
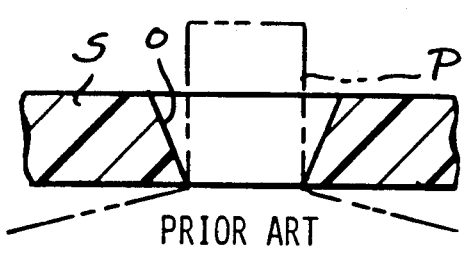
FIG. 4 is a cross-sectional view of an opening through the patient's skin formed by the method illustrated in FIG. 3.

The problem to which the present invention is directed is illustrated in FIGS. 3 and 4.

In order to cut a circular opening through the skin of a patient, a hollow cylindrical cutting tool or trephine T, sharpened at one end edge to form a circular cutting edge, is pushed downwardly through the skin S. The skin possesses a substantial amount of resilience, with the result that as the trephine is pressed downwardly against the skin as shown in FIG. 3, the skin will be deformed as shown, this effect being somewhat exaggerated in FIG. 3 for purposes of illustration. Pressure applied by the cutting edge of the trephine compresses the skin immediately beneath it and, to accommodate this compression, the skin will flow from beneath the cutting edges as indicated by the directional arrows in FIG. 3. Flow of skin radially inwardly from the cutting edge encounters some resistance since it is opposed by flow in the opposite direction from the diametrically opposite side of the cutting edge, while flow radially outwardly from the cutting edge is substantially unresisted. As a result, when the severed circular segment of skin is removed, it leaves an opening through the skin whose edge is inclined inwardly of the skin, as at 0 in FIG. 4, with the diameter of the opening at the outer surface of the skin being larger than that at the bottom of the opening.

Where this circular opening through the skin is cut to provide a passage through the skin for the projection P of a PAD indicated in broken line in FIG. 4, problems relating to the "fit" of the projection within opening 0 arise.

When an opening is cut through the skin, the outer layer of skin—that is, the epidermis—is stimulated to produce new epidermal cells along the edges of the openings until these new cells meet and grow together to close the opening. In the case of a circular opening, new epidermal cells will be produced at the periphery of the opening, and in the case where a solid object, such as the projection P of a PAD projects through the opening, the epidermis will tend to grow inwardly or downwardly along the side of the projection in an attempt to cover the severed edge of the underlying dermal layer.

U.S. Pat. No. 4,634,422 discloses means and methods for preventing this down growth by forming a multiplicity of microscopic openings or pores in the exposed surface of the projection P into which dermal cells can expand until a firm mechanical interlock is achieved between the dermal layer and projection P. U.S. Pat. No. 4,634,422 describes in detail a technique for culturing a multi-layer coating of dermal cells upon the microporous surface of the projection P prior to the implanting of the PAD in the patient so that, upon implantation, the dermal cells at the side of the opening can, within a relatively short time, grow into interlocking relationship with the coating of dermal cells on the PAD projection. Bonding of dermal cells to each other, as in the case of a minor cut, proceeds with sufficient rapidity so that ingrowth of the epidermal layer into the cut does not occur.

Assuming that a PAD of the type disclosed in U.S. Pat. No. 4,634,422, which has a cylindrical projection P, is to be implanted, an opening with an outwardly inclined edge as shown in FIG. 4 obviously does not provide optimum conditions for interlocking growth between dermal cells at the edge of the opening and the wall of the projection P. If, as indicated in FIG. 4, the diameter of the opening 0 at the inner side of the dermal layer of skin S is a reasonably close fit to the projection P, there is a gap of increasing width between the surface of projection P and the sidewall of the opening which is of maximum width at the outer surface of the skin. This gap will interfere with bonding between the underlying dermal layer of the skin and the projection P, afford an opportunity for at least some initial down growth of the outer epidermal layer with a consequent reduction in the ultimate bonding area between the dermal layer and projection P, and present a substantial risk of infection.

If, on the other hand, the diameter of the opening at the outer skin surface matches that of the projection P, insertion of the projection P through the opening from the inner side of the skin will tend to wipe off the dermal cells carefully cultured onto the microporous surface of the projection P prior to implantation.

In that the sidewalls of the opening cut by the trephine T through the skin taper inwardly from that side of the skin from which the cut was made, it is believed apparent that the direction of the taper shown in FIG. 4 would be reversed if the trephine had cut outwardly through the skin rather than inwardly as in FIG. 3. A tool for performing this operation is the subject matter of the present invention, and such a tool is shown in FIGS. 1 and 2 of the drawing.

The tool includes a hollow cylindrical housing designated generally 10 having a main bore 12 extending downwardly from its upper end to a shoulder 14 and a relatively small diameter counterbore 16 extending downwardly from shoulder 14 through the lower end of housing 10.

Figure 1:
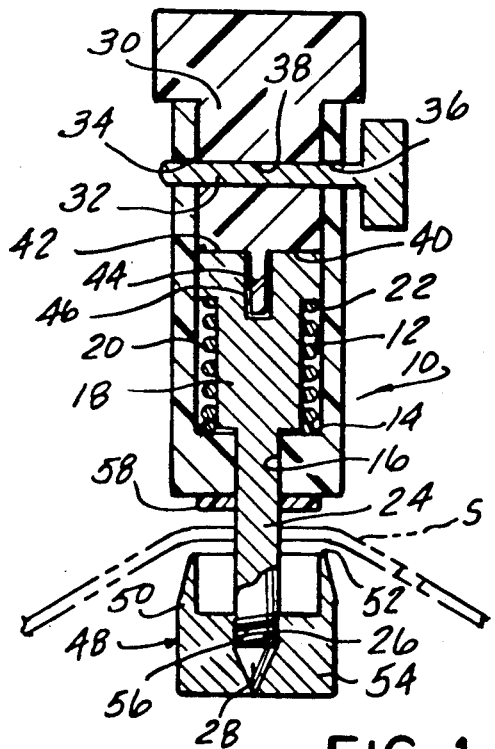
FIG. 1 is a cross-sectional view taken on an axial plane of a surgical tool embodying the present invention, showing the tool in a ready position.
Figure 2:
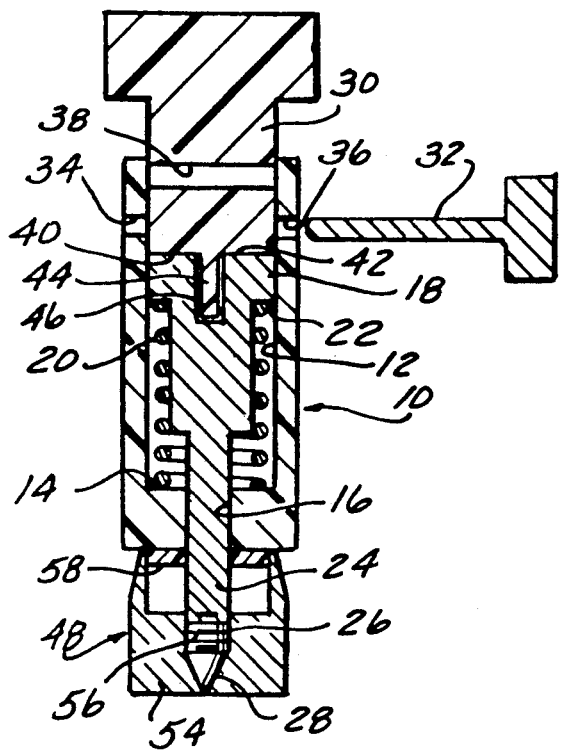
FIG. 2 is a view similar to FIG. 1 showing the tool in an actuated position.

Slidably received within main bore 12 is a plunger-like piston 18 spring biassed upwardly as viewed in FIGS. 1 and 2 by a compression spring 20 engaged between shoulder 14 of housing 10 and a downwardly facing shoulder 22 on piston 18. An elongate rod portion 24 of piston 18 is slidably received within counterbore 16 and projects downwardly from housing 10 to an externally threaded section 26 immediately above a conical guide portion 28 at the lower end of rod portion 24. A plug member 30 is, as best seen in FIG. 1, normally slidably received within the upper end of bore 12 and positively held in the seated position shown in FIG. 1 by a transverse locking pin 32 which passes through aligned bores 34, 36 at diametrically opposed positions in the sidewall of housing 10 and through a diametrical bore 38 in the plug member 30. The lower end 40 of plug member 30, when in its seated position shown in FIG. 1, abuts against the upper surface 42 of piston 18 to hold piston 18 at its lower end limit of movement relative to housing 10 with spring 20 firmly compressed from its normal relaxed position. A blade-like projection 44 integrally formed and projecting from the lower surface 40 of plug member 30 is, in FIG. 1, received within a diametrically extending slot 46 in the top of piston 18. The interengagement between the blade-like projection 44 and the opposed walls of slot 46 may be employed to rotate piston 18 within housing 10 by rotating plug member 30.

A cutting element or trephine designated generally 48 has a hollow cylindrical body 50 formed with a sharpened circular cutting edge 52 at its upper end and a relatively thick base portion or end wall 54 at its lower end. End wall 54 is formed with a centrally located threaded bore 56 by means of which trephine 48 may be threadably attached to rod portion 24 of piston 18 as shown in FIGS. 1 and 2. A washer-like backing element 58 is mounted on the lower end of housing 10 coaxially of rod portion 24. The outer peripheral edge of backing member 58 is of a diameter matched to that of the cutting edge 52 of trephine 48 to provide a shearing surface.

The tool described above is employed as follows:

As described in greater detail in U.S. Pat. No. 4,634,422, the preferred procedure for implanting a PAD in a patient is to first form a pocket beneath the skin for the reception of the PAD. This is done by cutting an incision through the skin and separating the skin from the underlying tissue at one side of the incision to form a pocket. A dummy PAD of the same size and general configuration of the PAD to be ultimately installed is then inserted into this pocket to be completely covered by unbroken skin. The incision is then closed for about a two-week healing period to allow the sides of the pocket to heal and conform themselves to the shape of the PAD. During this healing period, the dermal coating is being cultured on the projection of the PAD to be implanted.

At the conclusion of the healing period, the incision is opened and the dummy PAD removed. Prior to removal of the dummy PAD, a small hole may be punched through the skin centered on the top of the projection of the dummy PAD.

The trephine 48 of the tool described above is then unthreaded from its rod portion 24 and inserted into the pocket beneath the skin, cutting edge up. The trephine may be held by a hemostat so that the pointed end 28 of rod portion 24 can be passed downwardly through the small opening punched through the skin as described above, centered in the tapped bore 56 of the trephine and threaded into the trephine to reattach the trephine to rod portion 24 of the tool.

Locking pin 32 is then withdrawn to allow spring 20 to drive piston 18 upwardly within housing 10, the rod portion 24 of piston 18 carrying the trephine upwardly with it. Backing member 32 bears against the outer surface of the skin, and the cutting edge 52 of the trephine thus passes upwardly through the skin and past the peripheral edge of the backing member 58 until the cutting edge seats against the bottom of housing 10. In the event the cut is not complete, the trephine may be rotated by inserting projection 44 of the plug member into the slot 46 of the piston to rotate the piston as described above. The trephine is withdrawn simply by withdrawing it upwardly through the opening which it has cut through the skin.

Figure 5:
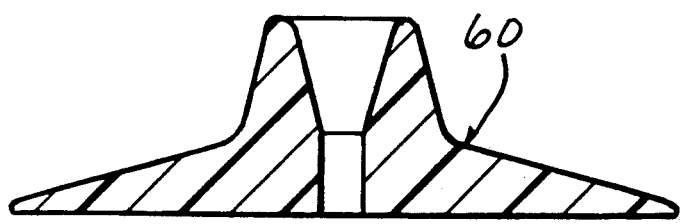
FIG. 5 is a cross-sectional view of a typical percutaneous access device.

As described above, the taper of the edge of the opening thus cut will taper inwardly toward the outer side of the skin, and the PAD 60 may be easily installed with a good fit between the edge of the opening and the projection P of the PAD 60. The inwardly tapering wall of the opening will provide a reasonably tight fit at the outer skin surface to the PAD and this taper will substantially match that of the conical-type PAD projection illustrated in FIG. 5. With a cylindrical projection, such as that on the PAD of U.S. Pat. NO. 4,634,422, the small diameter end of the opening through the skin is at the top, and thus upward movement of the PAD projection through the opening during implantation does not wipe any of the cultured dermal cells from that portion of the projection which will be opposed to the dermis when the implantation is completed.

While one embodiment of the invention has been described in detail, it will be apparent to those skilled in the art the disclosed embodiment may be modified. Therefore, the foregoing description is to be considered exemplary rather than limiting, and the true scope of the invention is that defined in the following claims:

We claim:

1. A surgical tool for cutting a circular opening through the skin of a patient with the diameter of the opening at the outer side of the skin being less than the diameter at the inner side of the skin, said tool comprising a cylindrical cup-shaped trephine having a circular cutting edge around its upper edge and a bottom wall having a centrally located threaded bore extending downwardly into said bottom wall, an elongate hollow cylindrical housing open at its upper end and having a lower end wall, a piston-like plunger slidably received in said housing for movement toward and away from said lower end wall, a rod fixed to said plunger and projecting coaxially from said housing through a bore through said lower end wall, the projecting end of said rod being threadably receivable in said threaded bore in said trephine, compression spring means in said housing resiliently biassing said plunger upwardly within said housing, and detachable stop means projecting into the upper end of said housing for normally maintaining said plunger at a lower end limit of movement relative to said end wall wherein said spring means exerts a maximum upward biassing force against said plunger.

2. The invention defined in claim 1 further comprising a washer-like backing member seated on the outer side of said lower end wall in coaxial relationship to said rod, said backing member having an outer peripheral edge dimensioned to slidably fit within said cutting edge of said trephine in shearing relationship therewith.

3. The invention defined in claim 1 wherein said stop means comprises a plug member insertable into said upper end of said housing to a seated position to depress said plunger within said housing to said lower end limit against the biassing action of said spring, and releasable locking means for releasably locking said plug member in said seated position.

4. The invention defined in claim 3 comprising means defining a tool receiving recess in the upper end of said plunger for receiving a tool operable to rotate said plunger within said housing.

5. The invention defined in claim 3 further comprising a projection on the end of said plug member seated in said recess when said plug member is in said seated position rotatively locking said plug member to said plunger.

6. The invention defined in claim 3 wherein said locking means comprises means defining diametrically opposed and aligned bores through the wall of said housing adjacent the upper end thereof, means defining a bore extending diametrically through said plunger, and a locking pin slidably received within and extending through said bores in the wall of said housing and the bore through said plunger.

7. The invention defined in claim 4 wherein said locking means comprises means defining diametrically opposed and aligned bores through the wall of said housing adjacent the upper end thereof, means defining a bore extending diametrically through said plunger, and a locking pin slidably received within and extending through said bores in the wall of said housing and the bore through said plunger.

8. The invention defined in claim 1 comprising means defining a tool receiving recess in the upper end of said plunger for receiving a tool operable to rotate said plunger within said housing.

* * * * *